United States Patent
Aoki et al.

(10) Patent No.: US 6,593,323 B1
(45) Date of Patent: Jul. 15, 2003

(54) BENZIMIDAZOLE COMPOUNDS AND DRUGS CONTAINING THE SAME

(75) Inventors: Kozo Aoki, Kanagawa (JP); Kazuhiro Aikawa, Kanagawa (JP); Masayuki Kawakami, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/019,562

(22) PCT Filed: Jun. 27, 2000

(86) PCT No.: PCT/JP00/04204
§ 371 (c)(1),
(2), (4) Date: Jun. 3, 2002

(87) PCT Pub. No.: WO01/00613
PCT Pub. Date: Jan. 4, 2001

(30) Foreign Application Priority Data

Jun. 30, 1999 (JP) ............................................. 11-185568

(51) Int. Cl.$^7$ ..................... A61K 31/5377; A61P 3/06; C07D 413/12; C07D 417/12
(52) U.S. Cl. .................... 514/230.8; 544/139; 546/199; 548/181; 548/226; 548/305.1; 548/306.1
(58) Field of Search .................................. 548/181, 226, 548/305.1, 306.1; 544/139, 230.8

(56) References Cited

U.S. PATENT DOCUMENTS 4,971,980 A  11/1990  Giani et al.

FOREIGN PATENT DOCUMENTS

| EP | 583665 A2 | 2/1994 |
| EP | 0 849 259 A1 | 6/1998 |
| EP | 0 987 254 A1 | 3/2000 |
| EP | 1 201 664 A1 | 5/2002 |
| WO | WO 95/34304 A1 | 12/1995 |
| WO | WO 97/03970 A1 | 2/1997 |
| WO | 98/54153 A1 | 12/1998 |
| WO | 99/25712 A1 | 5/1999 |

OTHER PUBLICATIONS

Tracy F. Gregory, et al. "Parallel Synthesis of a Series of Subtype–Selective NMDA Receptor Antagonists", Bioorganic & Medicinal Chemistry Letters, vol. 10, 2000, pp. 527–529.
Journal of Medicinal Chemistry, 35, (23), 4384–92, 1992.

Primary Examiner—Robert W. Ramsuer
(74) Attorney, Agent, or Firm—Sughrue Mion, PLLC

(57) ABSTRACT

A benzimidazole compound or a salt thereof which has an inhibitory action of forming of macrophages and is useful as an active ingredient of a medicament for preventive and/or therapeutic treatment of arteriosclerosis, which is represented by the formula (I):

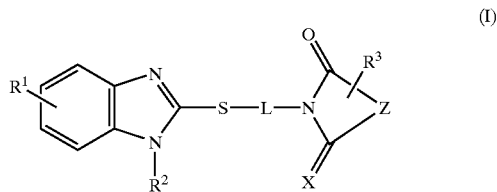

wherein, $R^1$ represents a functional group on the benzene ring selected from the group consisting of hydrogen atom, a halogen atom, a lower alkyl group and a lower alkoxy group; $R^2$ represents hydrogen atom, an alkyl group or an acyl group; $R^3$ represents a functional group on the ring containing the nitrogen atom and Z; Z represents a divalent group which forms a 5- or 6-membered ring; L represents a $C_4$–$C_8$ alkylene group or an ethyleneoxy linking group represented by $(CH_2CH_2O)_nCH_2CH_2$ wherein n represents 1 or 2; and X represents O or S.

17 Claims, No Drawings

BENZIMIDAZOLE COMPOUNDS AND DRUGS CONTAINING THE SAME

This application is a 371 of PCT/JP00/04204 filed Jun. 27, 2000.

TECHNICAL FIELD

The present invention relates to benzimidazole compounds useful as active ingredients of medicaments.

BACKGROUND ART

In recent years, patients with so-called adult diseases such as arterial sclerosis, hypertension, and diabetes mellitus have been continuously increasing with prolongation of life expectancy. In particular, patients with hyperlipidemia and arterial sclerosis derived therefrom have been remarkably increasing due to excessive intake of high calorie and high cholesterol food, which have become a serious social problem. Medications currently applied for treatment of hyperlipidemia and arterial sclerosis are those symptomatically lower cholesterol in blood, and no medicament that can be expected to have potency in retracting arterial sclerosis lesions has been used clinically. Arterial sclerosis is characterized by lesions of intimal hyperplasia and lipid accumulation in blood vessels, and it has been elucidated from recent biochemical findings that foaming of macrophages plays a main role in the formation of arterial sclerosis lesions. Accordingly, suppression of the foaming of macrophages may possibly prevent arterial sclerosis by inhibiting formation of arterial sclerosis lesions, or achieve radicular treatment of arterial sclerosis by retraction of arterial sclerosis lesions. However, no medicament having such activity has been known.

It has been suggested that an inhibitor of ACAT, an enzyme involved in intestinal absorption and metabolism of cholesterol, such as imidazole derivatives described in Bio. Med. Chem. Lett., Vol. 5(2), 167–172 (1995) reduces blood cholesterol level and thus suppresses the foaming of macrophages in an animal experiment (for example, piperazine derivatives described in International Publication WO98/54153). However, since these compounds are directed to ACAT inhibitory activity, they do not achieve satisfactory inhibition of the foaming of macrophages, and their effects are insufficient.

Therefore, an object of the present invention is to provide a compound having activity of suppressing the foaming of macrophages, and is useful as an active ingredient of a medicament for preventive and/or therapeutic treatment of arterial sclerosis. Another object of the present invention is to provide a compound having the aforementioned activity, and is useful as an active ingredient of medicament for preventive and/or therapeutic treatment of hyperlipidemia.

DISCLOSURE OF THE INVENTION

The inventors of the present invention conducted various researches to achieve the foregoing objects, and as a result, they found that novel benzimidazole compounds represented by the formula (I) set out below have activity of suppressing the foaming of macrophages, and are useful as active ingredients of preventive and/or therapeutic medicament of arterial sclerosis and preventive and/or therapeutic medicament of hyperlipidemia.

The compounds represented by the formula (I) according to the present invention have an inhibitory action against the foaming of macrophages independent from the ACAT inhibitory activity, and achieve remarkable effects in preventive and/or therapeutic treatment of arteriosclerosis based on the action. As benzimidazole compounds, available compounds include those known as active ingredients of medicaments for other applications (for example, the compounds of International Patent Publication WO95/34304) or those known as synthetic intermediates for drugs, agricultural chemicals or the like (for example, Chim. Chronika., Vol. 9(3), 239–246 (1980)). However, as demonstrated in the examples, the benzimidazole compounds known so far fail to inhibit the foaming of macrophages, and specific action of the compounds of the present invention are not suggested in view of these compounds.

The present invention thus provides benzimidazole compounds represented by the following formula (I):

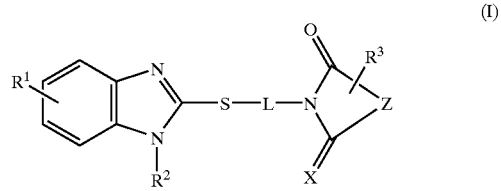

[in the formula, $R^1$ represents one or more functional groups on the benzene ring selected from the group consisting of hydrogen atom, a halogen atom, a lower alkyl group, and a lower alkoxy group; $R^2$ represents hydrogen atom, an alkyl group, or an acyl group; $R^3$ represents one or more functional groups on the ring containing the nitrogen atom and Z; Z represents a divalent group that forms a 5- or 6-membered ring; L represents a $C_4$–$C_8$ alkylene group or an ethyleneoxy linking group represented by $(CH_2CH_2O)_n CH_2CH_2$ (in the formula, n represents 1 or 2); and X represents O or S] and salts thereof.

The present invention also provides benzimidazole compounds represented by the following formula (II):

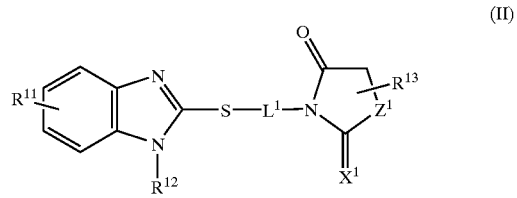

[in the formula, $R^{11}$ represents one or more functional groups on the benzene ring selected from the group consisting of hydrogen atom, a halogen atom, a lower alkyl group, and a lower alkoxy group; $R^{12}$ represents hydrogen atom, an alkyl group, or an acyl group; $R^{13}$ represents one or more functional groups on the ring selected from the group consisting of hydrogen atom, an alkyl group, an alkoxy group, an alkylthio group, an aryl group, and an acylamino group; $Z^1$ represents O, S, N, $CH_2O$, $OCH_2$, $CH_2S$, $SCH_2$, $CH_2NH$, or $NHCH_2$; $L^1$ represents a $C_4$–$C_8$ alkylene group; and $X^1$ represents O or S] and salts thereof.

As other aspects of the present invention, provided are methods for preparing the compounds represented by the aforementioned formula (I) or (II), and medicaments comprising a compound represented by the aforementioned formula (I) or (II) or a physiologically acceptable salt thereof as an active ingredient. As preferred embodiments of the aforementioned medicaments, pharmaceutical compositions are provided which comprise the aforementioned compounds or a physiologically acceptable salt thereof as an active ingredient and an additive for pharmaceutical preparation. The medicaments of the present invention are useful as, for example, those for preventive and/or therapeutic treatment of hyperlipidemia and for preventive and/or therapeutic treatment of arteriosclerosis. The medicaments are also useful as agents for suppressing foaming of macrophages, agents for retracting arterial sclerosis lesions, and agents for inhibiting formation of arteriosclerotic lesion.

As further aspects of the present invention, provided are uses of the compounds represented by the aforementioned formula (I) or (II) or salts thereof for manufacture of the aforementioned medicaments, and methods for preventive and/or therapeutic treatment of hyperlipidemia and methods for preventive and/or therapeutic treatment of arteriosclerosis, which comprise the step of administering a preventively and/or therapeutically effective amount of the compound represented by the aforementioned formula (I) or (II) or a physiologically acceptable salt thereof to a mammal including human.

BEST MODE FOR CARRYING OUT THE INVENTION

In the specification, a lower alkyl group or a lower alkyl moiety of a functional group that contains the lower alkyl moiety (e.g., lower alkoxy group) may be a linear, branched or cyclic alkyl group, or a combination thereof. For example, an alkyl group having 1–4 carbon atoms (for example, methyl group, ethyl group, n-propyl group, isopropyl group, n-butyl group, sec-butyl group, tert-butyl group and the like) may be used. A halogen atom referred to in the specification may be any of fluorine atom, chlorine atom, bromine atom and iodine atom.

An alkyl group or an alkyl moiety of a functional group that contains the alkyl moiety (e.g., an alkoxy group, an alkanoyl group, an alkylthio group and the like) referred to in the specification may be linear, branched or cyclic alkyl group or a combination thereof. An example includes an alkyl group having 1–8 carbon atoms (e.g., methyl group, ethyl group, butyl group, octyl group and the like), and a preferred example includes an alkyl group having 1–4 carbon atoms (e.g., methyl group, ethyl group, n-propyl group, n-butyl group). An aryl group or an aryl moiety of a functional group that contains the aryl moiety (arylcarbonyl group and the like) is preferably a monocyclic or bicyclic aryl group having a 6- to 10-membered ring, and more specifically, phenyl group, naphthyl group and the like can be used. An alkyl group or an alkyl moiety of a functional group having the alkyl moiety, a lower alkyl group or a lower alkyl moiety of the functional group having the lower alkyl moiety, or an aryl group may have one or two functional groups at any positions. When two or more functional groups exist, they may be the same or different.

Examples of the acyl group include an alkanoyl group, an arylcarbonyl group, an alkylsulfonyl group, an arylsulfonyl group, an alkoxycarbonyl group, a sulfamoyl group, a carbamoyl group and the like. Examples of the alkanoyl group include an alkanoyl group having 1–8 carbon atoms (e.g., acetyl group, butanoyl group, octanoyl group and the like), preferably an alkanoyl group having 1–4 carbon atoms (e.g., acetyl group, butanoyl group and the like). Examples of the arylcarbonyl group include an arylcarbonyl group having 6–10 carbon atoms (e.g., benzoyl group, naphthoyl group and the like). Examples of the alkoxycarbonyl group include an alkoxycarbonyl group having 1–8 carbon atoms (e.g., methoxycarbonyl group, ethoxycarbonyl group, octyloxycarbonyl group and the like), preferably an alkoxycarbonyl group having 1–4 carbon atoms (e.g., methoxycarbonyl group, ethoxycarbonyl group and the like).

Examples of the alkylsulfonyl group include an alkylsulfonyl group having 1–8 carbon atoms (e.g., methanesulfonyl group, butanesulfonyl group, octanesulfonyl group and the like) and examples of the arylsulfonyl group include an arylsulfonyl group having 6–10 carbon atoms (e.g., benzenesulfonyl group, naphthalenesulfonyl group and the like). Examples of the sulfamoyl group include a sulfamoyl group having 0–8 carbon atoms (e.g., sulfamoyl group, methylsulfamoyl group, diethylsulfamoyl group, octylsulfamoyl group, hexadecylsulfamoyl group, phenylsulfamoyl group and the like), preferably a sulfamoyl group having 0–4 carbon atoms (e.g., sulfamoyl group, methylsulfamoyl group, diethylsulfamoyl group and the like). Examples of the carbamoyl group include a carbamoyl group having 0–8 carbon atoms (e.g., carbamoyl group, methylcarbamoyl group, diethylcarbamoyl group, octylcarbamoyl group, hexadecylcarbamoyl group, phenylcarbamoyl group and the like), preferably a carbamoyl group having 0–4 carbon atoms (e.g., methylcarbamoyl group, diethylcarbamoyl group and the like). The aforementioned acyl group may have on or more functional groups at any position. When two or more functional groups exist, they may be the same or different.

$R^1$ represents one or more functional groups on the benzene ring selected from the group consisting of hydrogen atom, a halogen atom, a lower alkyl group, and a lower alkoxy group. When $R^1$ represents two or more functional groups, they may be the same or different, and substitution positions on the benzene ring are not also particularly limited. The halogen atom represented by $R^1$ may preferably be fluorine atom, chlorine atom, or bromine atom. $R^1$ may preferably be hydrogen atom, methyl group, methoxy group, or chlorine atom, and more preferably hydrogen atom.

$R^2$ is preferably hydrogen atom, a $C_1$–$C_4$ alkyl group, or a $C_1$–$C_4$ alkanoyl group, and most preferably hydrogen atom. L represents a linking group, and more specifically a $C_4$–$C_8$ alkylene group (e.g., butylene group, pentamethylene group, hexamethylene group, octamethylene group and the like) or an ethyleneoxy linking group represented by $(CH_2CH_2O)_nCH_2CH_2$ (in the formula, n represents 1 or 2). These linking groups may be linear or branched. The linking group represented by L is preferably a $C_5$–$C_8$ alkylene group (pentamethylene group, hexamethylene group, heptamethylene group, octamethylene group and the like) or the aforementioned ethyleneoxy bridging group, and most preferably a $C_5$–$C_8$ alkylene group.

X represents O or S, and particularly preferred X is O. The divalent group represented by Z contains 2 or 3 atoms constituting the 5- or 6-membered ring, and generally, the group is formed by a combination of atoms selected from the group consisting of a carbon atom, an oxygen atom, a sulfur atom, and a nitrogen atom. Specific examples thereof include, for example, —CH$_2$CH$_2$—, —CH$_2$CH$_2$CH$_2$—, —CH$_2$O—, —OCH$_2$—, —CH$_2$CH$_2$O—, —OCH$_2$CH$_2$—, —CH$_2$OCH$_2$—, —CH$_2$S—, —SCH$_2$—, —CH$_2$CH$_2$S—, —SCH$_2$CH$_2$—, —CH$_2$SCH$_2$—, —CH$_2$NH—, —NHCH$_2$—, —CH$_2$CH$_2$NH—, —NHCH$_2$CH$_2$—, —CH$_2$NHCH$_2$— and so forth. Examples of the ring containing the nitrogen atom and Z include, for example, succinimide, glutarimide, phthalimide, oxazolidine-2,4-dione, thiazolidine-2,4-dione, thiazolidin-4-one-2-thione, hydantoin, thiohydantoin, morpholine-3,5-dione, thiomorpholine-3,5-dione, 2,6-diketopiperazine, a dihydrouracil and the like.

$R^3$ represents one or more functional groups, including hydrogen atom, on the ring containing A and the nitrogen atom as ring constituting atoms. The type, substitution position, and number of the functional groups attached to the ring are not particularly limited. Plural functional groups represented by $R^3$ may bind to each other to form a saturated, partially saturated, or aromatic hydrocarbon ring, or a saturated, partially saturated, or aromatic heterocyclic ring containing one or more hetero atoms (e.g., nitrogen atom, oxygen atom, sulfur atom or the like) as ring constituting atoms. One or more functional groups represented by $R^3$ may be present on the divalent group represented by Z. Two of $R^3$ substituting on Z may bind to each other to form a saturated, partially saturated, or aromatic hydrocarbon ring, or a saturated, partially saturated or aromatic heterocyclic ring containing one or more hetero atoms (e.g., nitrogen atom, oxygen atom, sulfur atom and the like) as atoms constituting the ring.

Preferred examples of the functional groups represented by $R^3$ include an alkyl group (e.g., methyl group, ethyl group, butyl group, octyl group and the like), an alkoxy group (e.g., methoxy group, ethoxy group, benzyloxy group and the like), an alkylthio group (e.g., methylthio group, ethylthio group, octylthio group and the like), an aryl group (e.g., phenyl group, naphthyl group and the like), an acylamino group (e.g., acetylamino group, benzoylamino group, ureido group and the like) and so forth. When the functional groups substitute on a nitrogen atom as a ring constituting atom, the functional groups are preferably selected from an alkyl group and phenyl group. These functional groups may further be substituted with other functional groups. The ring containing the nitrogen atom and Z is preferably a ring not condensed with other ring.

Particularly preferred imidazole compounds are represented by the aforementioned formula (II). Preferred examples of $R^{11}$ and $R^{12}$ are the same as those explained as for the aforementioned $R^1$ and $R^2$, respectively. The alkylene group represented by $L^1$ may be linear or branched, and examples thereof include butylene group, pentamethylene group, hexamethylene group, octamethylene group and the like. The group is preferably an alkylene group having 5–8 carbon atoms (e.g., pentamethylene group, hexamethylene group, heptamethylene group, octamethylene group and the like), and most preferably an alkylene group having 5 or 6 carbon atoms.

$Z^1$ represents O, S, N, $CH_2O$, $OCH_2$, $CH_2S$, $SCH_2$, $CH_2NH$ or $NHCH_2$. Example of 5- or 6-membered imide and thioimide containing nitrogen atom and Z, include a succinimide (e.g., succinimide, 3-butylmercaptosuccinimide, 3-propionylaminosuccinimide and the like), a glutarimide (e.g., glutarimide, 3-ethyl-3-methylglutarimide, 3,3-tetramethyleneglutarimide and the like), phthalimide, an oxazolidine-2,4-dione (e.g., 5-methyloxazolidine-2,4-dione, 5,5-dimethyloxazolidine-2,4-dione and the like), thiazolidine-2,4-dione, thiazolidin-4-one-2-thione (e.g., rhodanine and the like), a hydantoin (e.g., hydantoin, 5-pentamethylenehydantoin, 5,5-dimethylhydantoin, 5,5-diphenylhydantoin, 1,5,5-trimethylhydantoin, 1-benzyl-5-ethoxyhydantoin, allantoin and the like), thiohydantoin, morpholine-3,5-dione, thiomorpholine-3,5-dione, 2,6-diketopiperazine, dihydrouracil and so forth. Examples of $R^{13}$ are the same as those explained as preferred examples of the aforementioned $R^3$.

$R^{11}$ is preferably hydrogen atom, methyl group, methoxy group or chlorine atom, and most preferably hydrogen atom. $R^{12}$ is preferably hydrogen atom, a $C_1$–$C_4$ alkyl group, and most preferably hydrogen atom. $X^1$ is preferably O. $Z^1$ is preferably O, S, N, $CH_2O$, or $OCH_2$, and the imide or thioimide ring containing the nitrogen atom and $Z^1$ is most preferably oxazolidine-2,4-dione, thiazolidine-2,4-dione, thiazolidine-4-one-2-thione, hydantoin, morpholine-3,5-dione or a derivative thereof.

Preferred compounds according to the present invention will be exemplified below. However, the scope of the present invention is not limited to these examples.

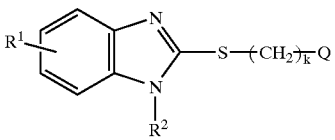

| No. | k | $R^1$ | $R^2$ | Q |
|---|---|---|---|---|
| 1 | 5 | H | H | 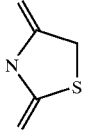 |
| 2 | 5 | H | H | 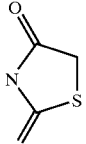 |
| 3 | 5 | H | H | 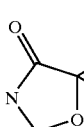 |
| 4 | 5 | H | H | 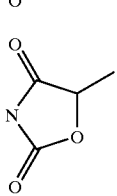 |
| 5 | 5 | H | H |  |
| 6 | 6 | H | H | 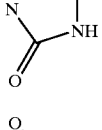 |
| 7 | 6 | H | H | 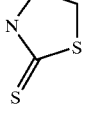 |

| No. | | | | |
|---|---|---|---|---|
| 8 | 6 | H | H | 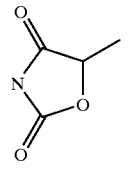 |
| 9 | 8 | H | H | 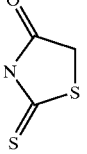 |
| 10 | 8 | H | H | 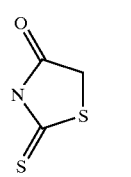 |
| 11 | 5 | H | H | 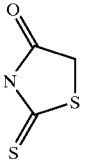 |
| 12 | 5 | H | H | 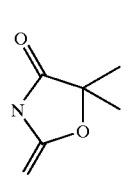 |
| 13 | 5 | H | H | 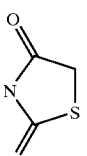 |
| 14 | 5 | H | CH$_3$ | 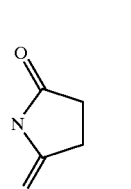 |
| 15 | 5 | H | COC$_2$H$_5$ | 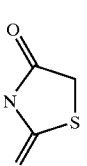 |
| 16 | 6 | 5-Cl | H | 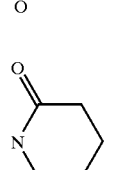 |
| 17 | 6 | 5-CH$_3$ | H | 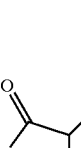 |
| 18 | 6 | 5-OCH$_3$ | H | 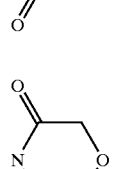 |
| 19 | 6 | 5,6-Cl$_2$ | H | 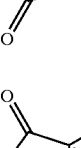 |
| 20 | 6 | H | H | 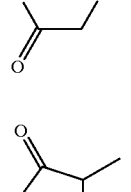 |
| 21 | 5 | H | H | 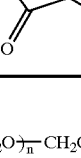 |
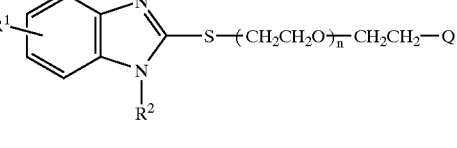
| No. | R$^1$ | R$^2$ | n | Q |
|---|---|---|---|---|
| 22 | H | H | 1 | 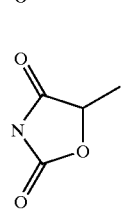 |

| | | | |
|---|---|---|---|
| 23 | H | H | 2 | 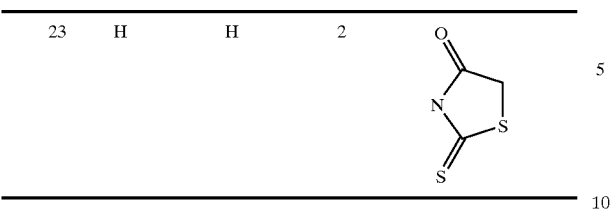 |

The compounds of the present invention represented by the aforementioned formulas (I) and (II) may form acid addition salts, and such acid addition salts fall within the scope of the present invention. Examples of the acid addition salts include, for example, mineral acid salts such as hydrochlorides, hydrobromides, nitrates, sulfates, and phosphates, and organic acid salts such as p-toluenesulfonates, methanesulfonates, oxalates, tartrates, malates, and citrates. Further, depending on the type of a functional group, they may also form base addition salts. Furthermore, the compounds of the present invention and salts thereof may exist as hydrates or solvates. Any of the compounds in free forms or in the forms of salts, and hydrates and solvates thereof falls within the scope of the present invention.

The compounds of the present invention may have one or more asymmetric carbons depending on the kind of a functional group. In such compounds, stereoisomers such as optical isomers based on one or more asymmetric carbons and diastereoisomers based on two or more asymmetric carbons may exist. Any of stereoisomers in pure forms, any mixtures of the stereoisomers, racemates and the like fall within the scope of the present invention.

The compounds of the present invention can be prepared from readily available raw material compounds by methods well known to those skilled in the art, for example, in accordance with the following scheme. Specific procedures of these methods are explained in detail in the examples of the specification, and those skilled in the art can easily produce the compounds of the present invention by referring to the general explanations given below and the examples, and by adding suitable alterations or modifications to these methods as required (the symbols used in the scheme have the same meanings as those defined above).

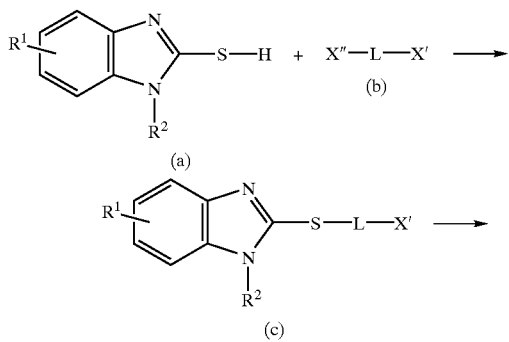

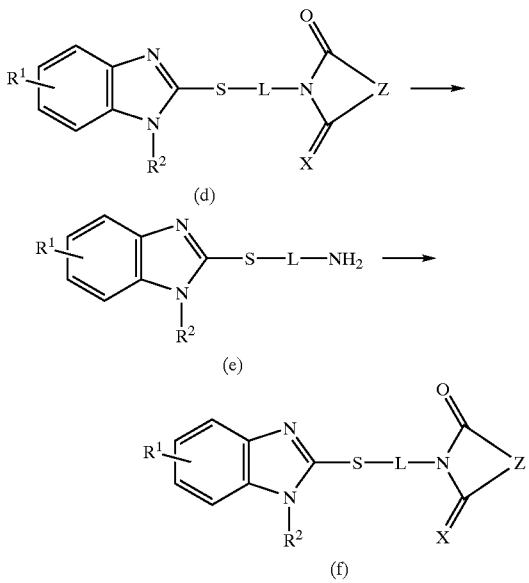

A 2-mercaptobenzimidazole derivative (a) and a compound (b) having a linking chain (L) (a bi-functional halogeno compound such as a chloride, bromide or iodide, or a sulfonate compound such as tosylate or methanesulfonate and the like, more specifically, dibromopentane, bis-2-chloroethyl ether and the like) to obtain a compound (c) in which one of the functional groups is replaced with the 2-mercaptobenzimidazole derivative. As a solvent, alcohols, acetonitrile and the like can be used, and reaction temperature may be from room temperature to 150° C., preferably about 50° to 120° C. Further, when a base such as triethylamine is used as an acid scavenger, the reaction may sometimes progress faster, thereby the reaction temperature may be lowered and the reaction time may be shortened.

The compound (b) wherein only one of the functional groups is a halide or sulfonate is subjected to the reaction (the remaining functional group may optionally be hydroxyl group, acetate moiety or the like, and the reaction condition for said compound may be the same as that mentioned above), and then the resulting compound (c) is subjected to substitution of X' with a halide or sulfonate. For example, substitution from hydroxyl group to a halide or sulfonate can be conducted by a conventional method utilizing tosyl chloride, carbon tetrabromide/triphenylphosphine or the like. The compound (c) as being a halide or sulfonate can be used as a key compound for a reaction with various imide derivatives, thioimide derivatives and the like to obtain a target compound (d). As a solvent, acetonitrile or dimethylformamide and the like can be used, and reaction temperature may be from room temperature to 150° C., preferably about 50° C. to 120° C. Further, when a base such as triethylamine or potassium carbonate is used as an acid scavenger, the reaction may sometimes progress faster, thereby the reaction temperature may be lowered and the reaction time may be shortened.

As an alternative method, a compound (c) as being a halide or sulfonate is reacted with potassium phthalimide to obtain a phthalimide (reaction conditions for this reaction are the same as those mentioned above) and the product can be hydrolyzed with hydrazine to obtain a compound (e) as being an amino compound. From the amino compound, a compound (f) as the target substance can be prepared by an ordinary method for preparation of an imide or hydantoin.

When an imide is desired, the amino compound can be reacted with a cyclic acid anhydride (the reaction can be performed at about 50° C. to 150° C., preferably 50° C. to 120° C. by using toluene, acetonitrile, tetrahydrofuran or the like as a solvent) and then heated to 80° C. or higher, preferably 100° C. to 160° C., in the presence of an acid catalyst (e.g., p-toluenesulfonic acid, sulfuric acid and the like) in an inert solvent (e.g., toluene, xylene and the like) to produce a compound (d). Further, the amino compound (e) can be condensed with a corresponding amino acid in a conventional manner and then condensed with carbonyl chloride, thiocarbonyl chloride or its equivalent compound for cyclization to produce a hydantoin.

The compounds of the present invention have a potent activity of suppressing the foaming of macrophages which is involved in the formation of arterial sclerosis lesions in arterial sclerosis. Therefore, the compounds are useful as an active ingredient of a medicament for preventive and/or therapeutic treatment of arterial sclerosis, and an active ingredient of a medicament for preventive and/or therapeutic treatment of hyperlipidemia by lowering blood cholesterol. Although it is not intended to be bound by any specific theory, it has been known that invasion of foamed macrophages into arterial walls triggers hyperplasia of smooth muscles of arterial walls, thereby causing arterial sclerosis (Schaffner, T. et al., Amer. J. Pathol., 110, pp.57–73, 1980; Gerrity, R. G., Amer. J. Pathol. 103, pp.181–190, 1981). The medicaments of the present invention directly inhibit the formation of arterial sclerosis lesions and enables retraction of arterial sclerosis lesions by suppressing the foaming of macrophages which is involved in the formation of arterial sclerosis lesions. Accordingly, the medicaments of the present invention are useful for prevention and/or treatment of arterial sclerosis and hyperlipidemia brought by various causes.

As the active ingredients of the medicaments of the present invention, a substance selected from the group consisting of the compounds represented by the aforementioned formula (I) and salts thereof, and hydrates thereof and solvates thereof can be used. Among the compounds represented by the formula (I), the compounds represented by the formula (II) are preferred. Routes of administration of the aforementioned medicament are not particularly limited, and they can be administered orally or parenterally. Oral administration is preferred. Although the aforementioned substance as the active ingredient, per se, may be used as the medicament of the present invention, it is generally desirable to provide the medicament as a pharmaceutical composition in a form well known to those skilled in the art by adding pharmaceutical additives as required.

Examples of the pharmaceutical composition suitable for oral administration include, for example, tablets, capsules, powders, subtilized granules, granules, solutions, syrups and the like. Examples of the pharmaceutical composition suitable for parenteral administration include, for example, injections, fusion drips, suppositories, inhalants, transdermal preparations, transmucosal preparations, patches and the like. As the pharmaceutical additives, excipients, disintegrating agents or dissolving aids, isotonic agents, pH modifiers, stabilizers, propellants, tackifiers and the like can be used, and they can optionally be used in combination.

For example, for the manufacture of the pharmaceutical composition suitable for oral administration, transdermal administration, or transmucosal administration, usable pharmaceutical additives include excipients such as glucose, lactose, D-mannitol, starch and crystalline cellulose; excipients or disintegrating aids such as carboxymethyl cellulose, starch and carboxymethyl cellulose calcium; binders such as hydroxypropyl cellulose, hydroxypropylmethyl cellulose, polyvinylpyrrolidone and gelatin; lubricants such as magnesium stearate and talc; coating agents such as hydroxypropylmethyl cellulose, sucrose, polyethylene glycol and titanium oxide; bases such as vaseline, liquid paraffin, polyethylene glycol, gelatin, kaoline, glycerol, purified water and hard fat and the like. Further, the pharmaceutical composition can also be produced by using pharmaceutical additives such as, for example, propellants such as frons, diethyl ether and compressed gases; tackifiers such as sodium polyacrylate, polyvinyl alcohol, methyl cellulose, polyisobutylene and polybutene; base fabrics such as cotton cloth, and plastic sheets and the like.

For preparation of the pharmaceutical composition suitable for injection or drip infusion, usable pharmaceutical additives include, for example, dissolving agents and dissolving aids that can form aqueous injections or injections that are dissolved upon use such as distilled water for injection, physiological saline and propylene glycol; isotonic agents such as glucose, sodium chloride, D-mannitol and glycerol; pH modifiers such as inorganic salts, organic acids, inorganic bases and organic bases and the like.

Doses of the medicament of the present invention are not particularly limited, and suitably chosen depending on dosage forms, purpose of administration, i.e., preventive and/or therapeutic purpose, the age, body weight, and symptoms of a patient and the like. For example, for intravenous administration, about 10 mg to 400 mg per day for an adult as the amount of an active ingredient can be administered, and for oral administration, about 10 mg to 800 mg per day for an adult as the amount of an active ingredient can be administered. Preferred doses for an adult are 10 mg to 100 mg per day and 10 mg to 300 mg per day, respectively, as the amount of an active ingredient. The medicament of the present invention may be administered once or several times a day, and any administration period may be applied depending on the age of a patient and improvement of symptoms and the like.

EXAMPLE

The present invention will be explained more specifically with reference to the following examples. However, the scope of the present invention is not limited to the following examples.

Example 1

Synthesis of 5-(benzimidazoyl-2-thio)pentyl Bromide 6.0 g of 2-mercaptobenzimidazole and 60 g of 1,5-dibromopentane were dissolved in 50 ml of ethanol and the mixture was refluxed under heating for 6 hours. After the solvent was evaporated under reduced pressure, the residue was digested with 50 ml of ethyl acetate and 50 ml of hexane to obtain about 12 g of solid. The solid was added with 100 ml of water and neutralized with aqueous sodium hydroxide. The deposited oil-soluble substance was extracted with ethyl acetate, washed with water and concentrated. The residue was purified by silica gel column chromatography (chloroform) to obtain 8.7 g of crude crystals. The crystals were recrystallized from ethanol to obtain 7.8 g of the target title compound (yield: 66%).

Melting point: 126–127° C.

MS (FAB$^+$): m/z 300 (MH$^+$)

Example 2

Synthesis of 3-(5-(benzimidazolyl-2-thio)pentyl)-2, 4-thiazolidinedione (Compound 2)

0.3 g of 5-(benzimidazoyl-2-thio)pentyl bromide and 0.12 g of 2,4-thiazolidinedione were added to a mixture of 2.5 ml of acetonitrile and 0.18 ml of triethylamine and the mixture was stirred under reflux for 8 hours. After cooling, the reaction mixture was added with water and extracted with ethyl acetate. The organic layer was washed with water and the solvent was evaporated under reduced pressure. The residue was purified by silica gel chromatography (ethyl acetate:methylene chloride=1:4) and crystallized from ethyl acetate/hexane to obtain 0.24 g of the title compound (yield: 72%).

$^1$H-NMR (CDCl$_3$): (ppm) 1.44 (m, 2H), 1.63 (m, 2H), 1.70 (m, 2H), 3.30 (t, 2H), 3.61 (t, 2H), 3.93 (s, 2H), 7.20 (m, 2H), 7.52 (m, 2H)

MS (FAB$^+$): m/z 336 (MH$^+$)

In the same manner as in Example 2, the following compounds were synthesized by changing the raw material.

(Compound 1) Purified by silica gel column chromatography (ethyl acetate:methylene chloride=1:5) and then crystallized from ethyl acetate/hexane, yield: 17%.

$^1$H-NMR (CDCl$_3$): (ppm) 1.56 (m, 2H), 1.78 (m, 4H), 3.27 (t, 2H), 3.39 (t, 2H), 4.02 (s, 2H), 7.23 (m, 2H), 7.59 (m, 2H)

MS (FAB$^+$): m/z 352 (MH$^+$)

(Compound 3) Crystallized from water-containing acetonitrile, yield: 95%.

$^1$H-NMR (CDCl$_3$): (ppm) 1.47 (m, 2H), 1.56 (s, 6H), 1.70 (m, 2H), 1.84 (m, 2H), 3.31 (t, 2H), 3.52 (t, 2H), 7.21 (m, 2H), 7.52 (m, 2H)

MS (FAB$^+$): m/z 348 (MH$^+$)

(Compound 4) Purified by silica gel column chromatography (ethyl acetate:methylene chloride=1:5) and then crystallized from ethyl acetate/hexane, yield: 36%.

$^1$H-NMR (CDCl$_3$): (ppm) 1.47 (m, 2H), 1.58 (d, 3H), 1.69 (m, 2H), 1.81 (m, 2H), 3.31 (t, 2H), 3.53 (t, 2H), 7.21 (m, 2H), 7.53 (m, 2H)

MS (FAB$^+$): m/z 334 (MH$^+$)

(Compound 5) Purified by silica gel column chromatography (ethyl acetate:methylene chloride=1:5) and then crystallized from acetonitrile, yield: 51%.

$^1$H-NMR (CDCl$_3$): (ppm) 1.47 (m, 2H), 1.70 (m, 2H), 1.78 (m, 2H), 3.25 (t, 2H), 3.57 (t, 2H), 5.05 (t, 1H), 7.20 (m, 2H), 7.39 (m, 5H), 7.50 (m, 2H)

MS (FAB$^+$): m/z 395 (MH$^+$)

(Compound 6) Purified by silica gel column chromatography (ethyl acetate:methylene chloride=1:5) and then crystallized from acetonitrile, yield: 46%.

$^1$H-NMR (CDCl$_3$): (ppm) 1.32 (m, 2H), 1.49 (m, 2H), 1.57 (m, 2H), 1.75 (m, 2H), 3.31 (t, 2H), 3.61 (t, 2H), 3.94 (s, 2H), 7.19 (m, 2H), 7.51 (be, 2H), 9.3 (br, 1H)

MS (FAB$^+$): m/z 350 (MH$^+$)

(Compound 7) Purified by silica gel column chromatography (ethyl acetate:methylene chloride=1:5) and then crystallized from ethyl acetate/hexane, yield: 33%.

$^1$H-NMR (CDCl$_3$): (ppm) 1.29 (m, 2H), 1.49 (m, 2H), 1.56 (s, 6H), 1.62 (m, 2H), 1.73 (m, 2H), 3.31 (t, 2H), 3.51 (t, 2H), 7.20 (m, 2H), 7.51 (br, 2H), 9.5 (br, 1)

MS (FAB$^+$): m/z 362 (MH$^+$)

(Compound 8) Purified by silica gel column chromatography (ethyl acetate:methylene chloride=1:5) and then crystallized from ethyl acetate/hexane, yield: 69%.

$^1$H-NMR (CDCl$_3$): (ppm) 1.34 (m, 2H), 1.52 (m, 2H), 1.58 (d, 3H), 1.63 (m, 2H), 1.73 (m, 2H), 3.31 (t, 2H), 3.53 (t, 2H), 4.83 (q, 1H), 7.20 (m, 2H), 7.33 (br, 1H), 7.67 (br, 1H), 9.33 (br, 1H)

MS (FAB$^+$): m/z 348 (MH$^+$)

(Compound 9) Purified by silica gel column chromatography (ethyl acetate:methylene chloride=1:5), solid, yield: 54%.

$^1$H-NMR (CDCl$_3$): (ppm) 1.29 (m, 6H), 1.41 (m, 2H), 1.57 (m, 2H), 1.75 (m, 2H), 3.32 (t, 2H), 3.60 (t, 2H), 3.94 (s, 2H), 7.19 (m, 2H), 7.33 (br, 1H), 7.69 (br, 1H), 9.6 (br, 1h)

MS (FAB$^+$): m/z 347 (MH$^+$)

(Compound 10) Purified by silica gel column chromatography (ethyl acetate:methylene chloride=1:5), oil, yield: 77%.

$^1$H-NMR (CDCl$_3$): (ppm) 1.27 (m, 6H), 1.42 (m, 2H), 1.56 (s, 3H), 1.61 (s, 3H), 1.63 (m, 2H), 1.73 (m, 2H), 3.33 (t, 2H), 3.51 (t, 2H), 7.19 (m, 2H), 7.50 (br, 2H), 9.35 (br, 2H)

MS (FAB$^+$): m/z 390 (MH$^+$)

(Compound 13) Purified by silica gel column chromatography (ethyl acetate:methylene chloride=1:5) and then crystallized from ethyl acetate/hexane, yield: 31%.

$^1$H-NMR (CDCl3): (ppm) 1.47 (m, 2H), 1.58 (m, 2H), 1.80 (m, 2H), 3.30 (t, 2H), 3.78 (t, 2H), 4.34 (s, 4H), 7.19 (m, 2H), 7.52 (br, 2H), 9.6 (br, 2H)

MS (FAB$^+$): m/z 334 (MH$^+$)

(Compound 20) Purified by silica gel column chromatography (hexane:ethyl acetate:=1:1), solid, yield: 33%.

$^1$H-NMR (CDCl3): (ppm) 1.33 (m, 2H), 1.7 (m, 2H), 1.60 (m, 2H), 1.74 (m, 2H), 3.26 (t, 2H), 3.60 (t, 2H), 7.55 (br, 2H)

MS (FAB$^+$): m/z 409 (MH$^+$)

Example 3

Synthesis of 2-(2-(2-chloroethoxy) ethylthiobenzimidazole)

6.0 g 2-mercaptobenzimidazole and 23 g of bis(2-chloroethyl) ether were dissolved in 45 ml of ethanol, and the mixture was added with 0.6 ml of triethylamine and refluxed for 15 hours. After the ethanol was evaporated under reduced pressure, the precipitates was added with 80 ml of ethyl acetate/hexane (1:1) for washing. The residue was dissolved in 20 ml of methanol and neutralized with aqueous sodium hydroxide. The deposited crystals were collected by filtration and washed with water/methanol (1:1) and dried to obtain 6.5 g of the title compound.

MS (FAB$^+$): m/z 257 (MH$^+$)

Example 4

Synthesis of 3-(2-(2-(benzimidazolyl-2-thio)ethoxy) ethyl-2,4-thiazolidinedione (Compound 23)

In an amount of 0.26 g of the 2-(2-(2-chloroethoxy) ethylthiobenzimidazole obtained in Example 3, 0.13 g of 2,4-thiazolidinedione and 0.07g of potassium iodide was added to a mixture of 2.5 ml of acetonitrile and 0.18 ml of triethylamine and then the mixture was stirred under reflux for 12 hours. After cooling, the reaction mixture was added with water and extracted with ethyl acetate. The organic layer was washed with water and the solvent was evaporated under reduced pressure. The residue was purified by silica gel chromatography (ethyl acetate:methylene chloride=1:4) and crystallized from ethyl acetate/hexane to obtain 0.24 g of title compounds (yield: 62%).

1H-NMR (CDCls): (ppm) 3.03 (t, 2H), 3.76 (t, 2H), 3.80 (t, 2H), 3.91 (t, 2H), 3.98 (s, 2H), 7.21 (m, 2H), 7.57 (br, 1H), 7.66 (br, 1H), 10.1 (br, 1H)

MS (FAB$^+$): m/z 338 (MH$^+$)

Example 5

Synthesis of 2-(2-(2-(2-chloroethoxy)ethoxy)ethylthiobenzimidazole)

12.0 g of 2-mercaptobenzimidazole and 60 g of bis(2-chloroethoxy)ethane were dissolved in 70 ml of ethanol, and the mixture was added with 1.0 ml of triethylamine and refluxed for 15 hours. After the ethanol was evaporated under reduced pressure, the precipitates were added with 80 ml of ethyl acetate/hexane (1:1) for washing. The residue was dissolved in 20 ml of methanol and neutralized with aqueous sodium hydroxide. The deposited oil was extracted with ethyl acetate and, after washing with water, the solvent was evaporated under reduced pressure. The residue was purified by silica gel column chromatography (methylene chloride) to obtain 16 g of the title compound.

MS (FAB$^+$): m/z 285 (MH$^+$)

Example 6

Synthesis of 3-(2-(2-(2-benzimidazolyl-2-thio)ethoxy)ethoxy)ethyl-2,4-thiazolidinedione (Compound 23)

0.30 g of the 2-(2-(2-(2-chloroethoxy)ethoxy)ethylthiobenzimidazole, 0.13 g of 2,4-thiazolidinedione and 0.07 g of potassium iodide were added to a mixture of 2.5 ml acetonitrile and 0.18 ml of triethylamine and then the mixture was stirred under reflux for 12 hours. After cooling, the reaction mixture was added with water and extracted with ethyl acetate. After washing with water, the solvent was evaporated under reduced pressure and the residue was purified by silica gel chromatography (ethyl acetate:methylene chloride 1:4) to obtain 0.18 g of the title compound as oil (yield: 47%).

$^1$H-NMR (CDCl$_3$): (ppm) 3.33 (t, 2H), 3.73 (s, 4H), 3.76 (s, 2H), 3.77 (m, 2H), 3.87 (m, 4H), 7.21 (m, 2H), 7.33 (br, 1H), 7.64 (br, 1H), 10.6 (br, 1H)

MS (FAB$^+$): m/z 382 (MH$^+$)

Example 7

Synthesis of N-(5-(benzimidazolyl-2-thio)pentyl)succinimide (Compound 11)

0.45 g of 5-(benzimidazoyl-2-thio)pentyl bromide, 0.16 g of succinimide and 0.27g of potassium carbonate were added with 3 ml of DMF and then the mixture was stirred at 100° C. for 2 hours. After cooling, the reaction mixture was added with water and extracted with ethyl acetate. After washing with water, the solvent was evaporated under reduced pressure and the residue was purified by silica gel column chromatography (ethyl acetate:methylene chloride= 1:5) and further crystallized from ethyl acetate/hexane to obtain 0.28 g of the title compound (yield: 88%).

$^1$H-NMR (CDCl$_3$): (ppm) 1.44 (m, 2H), 1.59 (m, 2H), 1.80 (m, 2H), 2.71 (s, 4H), 3.28 (t, 2H), 3.51 (t, 2H), 7.20 (m, 2H), 7.36 (br, 1H), 7.69 (br, 1H), 9.63 (be, 1H)

MS (FAB$^+$): m/z 318 (MH$^+$)

In the same manner as in Example 7, the following compounds were synthesized.

(Compound 12) Purified by silica gel column chromatography (ethyl acetate:methylene chloride=1:5) and then crystallized from ethyl acetate/hexane, yield: 23%.

$^1$H-NMR (CDCl3): (ppm) 1.46 (m, 2H), 1.58 (m, 2H), 1.80 (m, 2H), 2.04 (m, 2H), 2.60 (t, 4H), 3.30 (t, 2H), 3.68 (t, 2H), 7.19 (m, 2H), 7.52 (br, 2H), 9.6 (br, 2H)

MS (FAB$^+$): m/z 334 (MH$^+$)

(Compound 21) Purified by silica gel column chromatography (ethyl acetate:methylene chloride=1:5) and then crystallized from ethyl acetate/hexane, yield: 87%.

$^1$H-NMR (CDCl$_3$): (ppm) 1.53 (m, 2H), 1.73 (m, 2H), 1.84 (m, 2H), 3.31 (t, 2H), 3.70 (t, 2H), 7.20 (m, 2H), 7.2 (m, 2H), 7.71 (m, 2H), 7.85 (m, 2H)

MS (FAB$^+$): m/z 366 (MH$^+$)

Example 8

Synthesis of 3-(5-(1-methylbenzimidazolyl-2-thio)pentyl)-5-methyl-2,4-oxazolidinedione (Compound 14)

0. 27 g of (Compound 4), 0.33 g of potassium carbonate and 0.14 g of methyl iodide were added with 1.5 ml of DMF and then the mixture was stirred at 50° C. for 3 hours. The reaction mixture was added with water and extracted with ethyl acetate, and after washing with water, the solvent was evaporated under reduced pressure. The residue was purified by silica gel chromatography (ethyl acetate:methylene chloride=1:9) to obtain 0.17 g of the title compound as oil (yield: 61%).

$^1$H-NMR (CDCl$_3$): (ppm) 1.57 (m, 2H), 1.70 (m, 2H), 1.85 (m, 2H), 3.40 (t, 2H), 3.57 (t, 2H), 3.69 (s, 3H), 7.21 (m, 3H), 7.66 (br, 1H)

MS (FAB$^+$): m/z 347 (MH$^+$)

Example 9

Synthesis of 3-(5-(1-propionylbenzimidazolyl-2-thio)pentyl)-5-methyl-2,4-oxazolidinedione (Compound 15)

0.27 g of (Compound 4) was dissolved in 1 ml of dimethylacetamide and 2 ml of acetonitrile, and then the mixture was added with 0.17 ml of triethylamine, and further added with 0.08 ml of propionyl chloride and stirred at 50° C. for 1 hour. The reaction mixture was added with water and extracted with ethyl acetate. The organic layer was washed with water, and then the solvent was evaporated under reduced pressure. The residue was purified by silica gel chromatography (ethyl acetate:methylene chloride=1:9) to obtain 0.28 g of the title compound as oil (yield: 90%).

$^1$H-NMR (CDCl$_3$): (ppm) 1.38 (t, 3H), 1.57 (m, 2H), 1.70 (m, 2H), 1.86 (m, 2H), 3.10 (q, 2H), 3.32 (t, 2H), 3.56 (t, 2H), 7.26 (m, 3H), 7.66 (br, 1H)

MS (FAB$^+$): m/z 390 (MH$^+$)

Example 10

Synthesis of 3-(6-(5-chlorobenzothiazolyl-2-thio)hexyl)-2,4-thiazolidinedione (Compound 16)

Example 10a 3-(6-Bromohexyl)-2,4-thiazolidinedione 36.6 g of 1,6-dibromohexane, 5.9 g of 2,4-thiazolidinedione and 7.1 g of triethylamine were added to 125 ml of acetonitrile and the mixture was heated with stirring under reflux for 8 hours. After cooling to room temperature, the solvent was evaporated under reduced pressure and the residue was poured into water. The mixture was extracted with methylene chloride and the methylene chloride layer was washed with saturated brine and dried over sodium sulfate. After the solvent was evaporated under reduced pressure, the residue was purified by silica gel column chromatography (hexane:ethyl acetate=5:1→4:1) to obtain 9.8 g of the title compound as pale yellow oil (yield: 70%).

Example 10b 3-(6-(5-Chlorobenzothiazolyl-2-thio)hexyl)-2,4-thiazolidinedione (Compound 16)

0.28 g of the compound obtained by Example 10a, 0.2 g of 5-chloro-2-mercaptobenzothiazole and 0.14 g of triethylamine were added to 2.5 ml of acetonitrile and then the mixture was heated under reflux with stirring for 8 hours. The reaction mixture was cooled to room temperature and poured into 50 ml of saturated aqueous sodium hydrogencarbonate. The mixture was extracted with ethyl acetate and the ethyl acetate layer was washed with saturated brine and dried over sodium sulfate. After the solvent was evaporated under reduced pressure, the residue was purified by silica gel column chromatography (hexane:ethyl acetate=2:1) to obtain 0.3 g of the title compound as white crystals (yield: 78%).

$^1$H-NMR (CDCl$_3$): (ppm) 1.30–1.42 (m, 2H), 1.45–1.56 (m, 2H), 1.57–1.70 (m, 2H), 1.80 (q, 2H), 3.3 (t, 2H), 3.62 (t, 2H), 3.96 (s, 2H), 7.27 (d, 1H), 7.63 (dd, 1H), 7.87 (d, 1H)

In the same manner as in Example 10b, the following compounds were synthesized by changing the raw material.

(Compound 17) Purified by silica gel column chromatography (ethyl acetate:methylene chloride=1:5), oil, yield: 82%.

$^1$H-NMR (CDCl$_3$): (ppm) 1.20–1.31 (m, 2H), 1.33–1.44 (m, 2H), 1.52 (q, 2H), 1.67 (q, 2H), 3.23 (t, 2H), 3.56 (t, 2H), 3.80 (s, 3H), 3.92 (s, 2H), 6.83 (dd, 1H), 7.02 (brs, 1H), 7.40 (d, 1H)

MS (FAB$^+$): m/z 380 (MH$^+$)

(Compound 18) Purified by silica gel column chromatography (ethyl acetate:methylene chloride=1:5), oil, yield: 94%.

$^1$H-NMR (CDCl$_3$): (ppm) 1.23–1.32 (m, 2H), 1.34–1.47 (m, 2H), 1.55 (q, 2H), 1.70 (q, 2H), 2.43 (s, 3H), 3.25 (t, 2H), 3.58 (t, 2H), 3.93 (s, 2H), 7.00 (d, 1H), 7.28 (brs, 1H), 7.40 (brs, 1H)

MS (FAB$^+$): m/z 364 (MH$^+$)

(Compound 19) Purified by silica gel column chromatography (ethyl acetate:methylene chloride=1:5), oil, yield: 79%

$^1$H-NMR (CDCl3): (ppm) 1.27–1.38 (m, 2H), 1.40–1.53 (m, 2H), 1.60 (q, 2H), 1.74 (q, 2H), 3.23 (t, 2H), 3.60 (t, 2H), 3.97 (s, 2H), 7.55 (brs, 2H)

MS (FAB$^+$): m/z 418 (MH$^+$)

Test Example 1

Activity of the compounds of the present invention for suppressing the foaming of macrophages, which triggers arterial sclerosis, was examined. (1) In vitro experiment using mouse peritoneal macrophages.

15-Week old female ICR mice (Nippon SLC) were subjected to bleeding by cutting off their cervicalis, and Hanks buffer (Nippon Seiyaku) was injected into their peritoneal cavities. After abdominal regions of the mice were massaged, the buffer was recovered immediately, and then the resulting buffer was centrifuged at 1,000 r.p.m. for five minutes to collect peritoneal macrophages. Then, the collected macrophages were suspended in GTI medium (Wako Pure Chemical Industries), and inoculated onto a 24-well microtiter plate. After the macrophages were cultivated at 37° C. under 5% CO$_2$ for two hours, the culture medium was changed with Dulbecco Modified Eagle Medium (MEM, Nippon Seiyaku). The macrophages were further cultivated at 37° C. under 5% CO$_2$ for 16 hours, and then a test compound and liposomes were added to the culture.

1) Test compound: dissolved in DMSO (Wako Pure Chemical Industries),
2) Liposomes: PC/PS/DCP/CHOL=50/50/10/75 (nmol)
   PC: Phosphatidylcholine (Funakoshi);
   PS: Phosphatidylserine (Funakoshi);
   DCP: Dicetylphosphate (Funakoshi);
   CHOL: Cholesterol (Sigma)

After cultivation was further continued at 37° C. under 5% CO$_2$ for 16 hours, lipid fraction was extracted with chloroform and methanol. The extracted lipid fraction was dissolved in isopropyl alcohol, and the produced cholesterol ester (CE) was quantified by an enzymatic luminescence method. Yield of the cholesterol ester was calculated as a relative ratio based on yield of the control as 100% where no test compound was added.

| Compound | Dose | CE yield (%) |
|---|---|---|
| (1) | 5 μM | 4.2 |
| (2) | 5 μM | 19 |
| (3) | 5 μM | 14 |
| (4) | 5 μM | 3.8 |
| (5) | 5 μM | 3.2 |
| (6) | 5 μM | 2.1 |
| (7) | 5 μM | 2.6 |
| (8) | 5 μM | 15 |
| (9) | 5 μM | 16 |
| (10) | 5 μM | 6.2 |
| (11) | 5 μM | 19 |
| (12) | 5 μM | 22 |
| (13) | 5 μM | 3.6 |
| (14) | 5 μM | 20 |
| (15) | 5 μM | 12 |
| (16) | 5 μM | 15 |
| (17) | 5 μM | 11 |
| (18) | 5 μM | 18 |
| (19) | 5 μM | 20 |
| (20) | 5 μM | 2.4 |
| (21) | 5 μM | 28 |
| (22) | 5 μM | 23 |
| (23) | 5 μM | 22 |
| (Ref. 1) | 5 μM | 89 |
| (Ref. 2) | 5 μM | 95 |
| (Ref. 3) | 5 μM | 78 |

(Ref. 1)

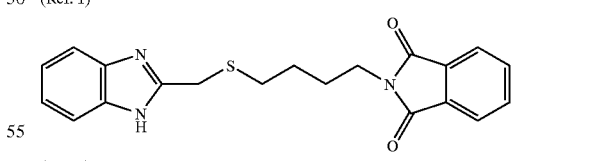

(Ref. 2)

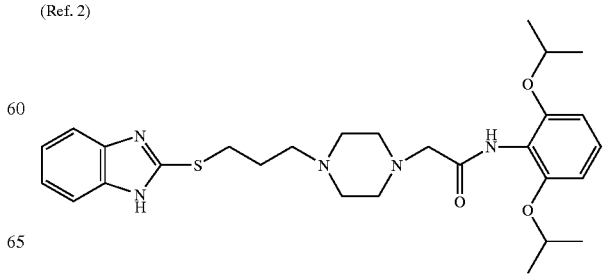

-continued

| Compound | Dose | CE yield (%) |
|---|---|---|

(Ref. 3)

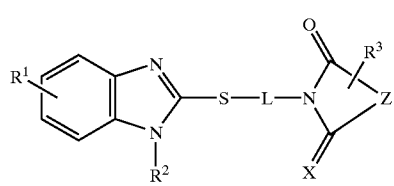

(Ref. 1) A synthesis intermediate described in J. Chem. Soc., Dalton Trans, (6), 1161 (1989)
(Ref. 2) Compound (9) described in International Patent Publication WO98/54153
(Ref. 3) Compound (3) described in Bio. Med. Chem. Lett., Vol. 5 (2), 167–172 (1995)

From these results, it is clearly understood that the compounds of the present invention acted on macrophases and remarkably reduced the rate of cholesterol ester synthesis (a smaller value means a more potent suppression, and 100% indicates no suppression, specifically, the results are interpreted as: effective for 30% or less, particularly potent effect for 10% or less, and completely no effect for 70% or more). Whilst, the known benzimidazole derivative having a phthalimide group used for comparison, i.e., the compound of (Ref. 1) having a benzimidazole structure similar to that of the compounds of the present invention, however, was found to be completely inactive in suppression of macrophages. Further, although the compounds of (Ref. 2) and (Ref. 3) are structurally similar benzimidazole derivatives, they exerted almost no inhibitory effect on macrophages.

INDUSTRIAL APPLICABILITY

The benzimidazole derivatives of the present invention have an action of suppressing the foaming of macrophages, and are useful as active ingredients of medicaments for preventive and/or therapeutic treatment of arteriosclerosis or medicaments for preventive and/or therapeutic treatment of hyperlipidemia. Further, they are also useful as additives for silver halide photosensitive materials or for the production of liquid crystals.

What is claimed is:

1. A benzimidazole compound represented by the following formula (I) or salt thereof:

(I)

![Structure I]

wherein, $R^1$ represents one or more functional groups on the benzene ring selected from the group consisting of a hydrogen atom, a halogen atom, a lower alkyl group, and a lower alkoxy group; $R^2$ represents a hydrogen atom, an alkyl group, or an acyl group; $R^3$ represents one or more functional groups on the ring containing the nitrogen atom and Z; Z represents a divalent group which forms a 5- or 6-membered ring; L represents a $C_4$–$C_8$ alkylene group or an ethyleneoxy linking group represented by $(CH_2CH_2O)_n CH_2CH_2$ wherein n represents 1 or 2; and X represents O or S.

2. The compound or a salt thereof according to claim 1, wherein the ring containing Z is a 5- or 6-membered ring not condensed with another ring.

3. The compound or a salt thereof according to claim 1, wherein $R^1$ and $R^2$ each represents a hydrogen atom.

4. The compound or a salt thereof according to claim 1, wherein L is a $C_4$–$C_8$ alkylene group.

5. The compound or a salt thereof according to claim 4, wherein L is a $C_5$ or $C_6$ alkylene group.

6. A benzimidazole compound represented by the following formula (II) or a salt thereof:

(II)

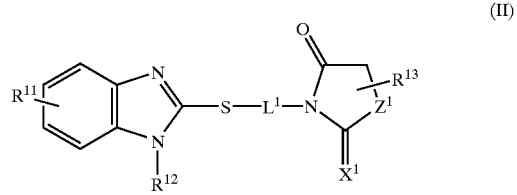

wherein, $R^{11}$ represents one or more functional groups on the benzene ring selected from the group consisting of a hydrogen atom, a halogen atom, a lower alkyl group, and a lower alkoxy group; $R^{12}$ represents a hydrogen atom, an alkyl group, or an acyl group; $R^{13}$ represents one or more functional groups on the ring selected from the group consisting of a hydrogen atom, an alkyl group, an alkoxy group, an alkylthio group, an aryl group, and an acylamino group; $Z^1$ represents O, S, N, $CH_2O$, $OCH_2$, $CH_2S$, $SCH_2$, $CH_2NH$, or $NHCH_2$; $L^1$ represents a $C_4$–$C_8$ alkylene group; and $X^1$ represents O or S.

7. The compound or a salt thereof according to claim 6, wherein each of $R^{11}$ and $R^{12}$ represents a hydrogen atom.

8. The compound or a salt thereof according to claim 6, wherein the ring containing the nitrogen atom and $Z^1$ in the formula (II) is oxazolidine-2,4dione, thiazolidine-2,4dione, thiazolidin-4-one2-thione, hydantoin, morpholine-3,5-dione, or a derivative thereof.

9. The compound or a salt thereof according to claim 6, wherein $L^1$ is a $C_4$–$C_8$ alkylene group.

10. The compound or a salt thereof according to claim 9, wherein $L^1$ is a $C_5$ or $C_6$ alkylene group.

11. A pharmaceutical composition comprising a compound represented by the following formula (I) or a physiologically acceptable salt thereof as an active ingredient and a pharmaceutical additive:

(I)

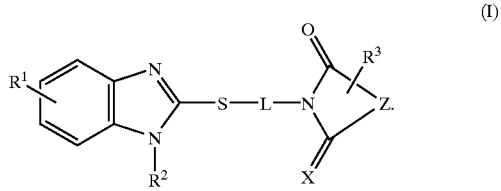

12. A pharmaceutical composition comprising a compound represented by the following formula (II) or a physiologically acceptable salt thereof as an active ingredient and a pharmaceutical additive:

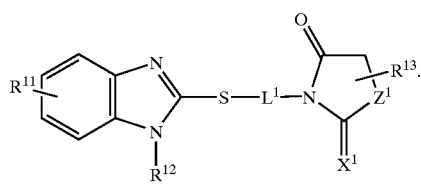
(II)

13. A method for preventing or treating hyperlipidemia, which comprises administering an effective amount of a composition according to claim 11 or 12 to a mammal.

14. A method for suppressing foaming of a macrophage, which comprises administering an effective amount of a composition according to claim 11 or 12 to a mammal.

15. A method for retracting arterial sclerosis lesions, which comprises administering an effective amount of a composition according to claim 11 or 12 to a mammal.

16. A method for inhibiting formation of arterial sclerosis lesions, which comprises administering an effective amount of a composition according to claim 11 or 12 to a mammal.

17. A method for preventing or treating arteriosclerosis, which comprises administering an effective amount of a composition according to claim 11 or 12 to a mammal.

* * * * *